United States Patent [19] [11] 4,255,267
Hoehn et al. [45] Mar. 10, 1981

[54] SEPARATION AND RECOVERY OF GRANULOCYTES FROM BLOOD USING ADHERENCE ON AN EXPANDABLE BED OF A POLYMERIC MATERIAL

[75] Inventors: Harvey H. Hoehn, Hockessin, Del.; John R. Wells, Culver City, Calif.

[73] Assignee: E. I. Du Pont de Nemours and Company, Wilmington, Del.

[21] Appl. No.: 90,678

[22] Filed: Nov. 2, 1979

[51] Int. Cl.³ .............................................. B01D 15/00
[52] U.S. Cl. ................................... 210/678; 210/692; 210/927
[58] Field of Search ............... 128/214 R; 210/20, 24, 210/30 R, 35, 40, 80–82, DIG. 23

[56] References Cited

U.S. PATENT DOCUMENTS

| | | | |
|---|---|---|---|
| 2,136,660 | 11/1938 | Martin | 210/80 |
| 2,682,268 | 6/1954 | Ryan et al. | 210/24 |
| 3,462,361 | 8/1969 | Greenwalt et al. | 210/24 |
| 3,802,432 | 4/1974 | Djerassi | 128/214 R |
| 3,929,130 | 12/1975 | Hargest | 128/214 R |
| 4,050,451 | 9/1977 | Columbus | 210/DIG. 23 |

OTHER PUBLICATIONS

Rabinowitz, "Separation of Lymphocytes, Polymorphonuclear Leukocytes and Monocytes on Glass Columns, Including Tissue Culture Observations," Blood, vol. 23, No. 6, (Jun.), 1964, pp. 811–828.

Primary Examiner—Ivars C. Cintins

[57] ABSTRACT

A leukapheresis process is disclosed in which an expandable bed of synthetic polymeric packing having a diameter of from 90 μm to 2000 μm and preferably 200 μm to 400 μm is used to adhere granulocytes from blood. The granulocytes are harvested from the packing by expanding the bed and washing with a physiologically acceptable solution.

11 Claims, No Drawings

SEPARATION AND RECOVERY OF GRANULOCYTES FROM BLOOD USING ADHERENCE ON AN EXPANDABLE BED OF A POLYMERIC MATERIAL

BACKGROUND OF THE INVENTION

1. Field of the Invention

The present invention relates to the recovery of granulocytes from human blood by a procedure which is commonly known as filtration leukapheresis. The isolated granulocytes are transfused into patients who have a low white cell count (neutropenia), and therefore are at increased risk to infection, are infected, or are not responding to antibiotics. This type of granulocyte support has been used clinically for more than 15 years. Recently, with the increase use of chemotherapy in the treatment of cancer, the need for white cell therapy has risen sharply because the drugs used also reduce the capacity of the bone marrow to produce granulocytes.

2. State of the Prior Art

Human blood is usually separated into various cellular components and plasma by centrifugation. However, centrifugal techniques for isolation of granulocytes requires expensive equipment and usually demand a high level of skill on the part of the operator of the centrifuge. For this reason, the simpler approach of filtration leukapheresis has important advantages for separation of granulocytes. The present commercial filtration leukapheresis system utilizes a cylindrical container (pack) filled tightly with short lengths (1.5") of nylon fiber. Generally when anti-coagulated whole blood is passed through the pack a portion of the granulocytes and some mononuclear cells adhere to the nylon fiber packing. The granulocytes are subsequently eluted from the packed fiber column by backwashing the column with a solution containing a chelating agent. In order to further facilitate elution of cells from the column, the pack is also tapped vigorously. This type of pack is disclosed in U.S. Pat. No. 3,462,361.

SUMMARY OF THE INVENTION

The present invention relates to the use of an expandable column containing a polymeric packing for harvesting granulocytes from anticoagulated whole blood. The column packing is enclosed in a suitable container such as a flexible cylinder or pack and the anticoagulated whole blood is passed over the column. A portion of the granulocytes adhere to the surface of the packing either directly or by adhesion to other granulocytes which are in turn adhered to the polymer surface. After the blood has been passed over the column, the granulocytes are removed with a suitable eluting solution. The present invention enables a higher recovery of granulocytes per unit of blood processed by virtue of a more efficient elution of these cells which have been adsorbed from the blood than is currently achieved using a pack containing randomly oriented fibers.

More complete recovery of adherent cells results from increasing the volume of the assembly containing the adsorbent polymer packing during treatment with eluant. This volume expansion can be accomplished by use of an expandable, e.g., accordion type, flexible container. Increasing the volume of the column during backwashing to the extent of at least 25% and generally to 50 to 600% compared to the volume during passage of blood through the column is responsible for the higher recovery of adhered cells. This technique applies equally well when granules, fibers, or rods of polymer are used as the column packing. When performing filtration leukapheresis and returning the granulocyte lean blood to the donor using conventional nylon fiber filled pack, the operation generally takes between 3 and 4 hours. The present invention can provide for a reduction in this time because higher percentages of the granulocytes are recovered.

DETAILED DESCRIPTION

In the present invention adhesion leukapheresis of blood is performed using a polymeric material (beads or an expandable fiber bundle) as the solid support medium. The granulocytes become attached to the fibers, rods or beads as the blood is passed through the bed of polymeric material. After the desired amount of blood has been passed through the pack, granulocytes are harvested by washing the bed with a physiologically acceptable solution containing a chelating agent which binds $Ca^{++}$, the result being that the granulocytes are released from the surface of the polymer.

The use of beads as the column material allows the bed to be expandable by backwashing or by inverting the container and allowing the beads to fall through the washing fluid. Alternatively when using a fiber bed the bed is expanded and backwashed. Cell adherent polymer packed in a column having accordion pleated sides is readily expandable and suitable for use herein.

In the continuous-flow filtration leukapheresis procedure, blood is withdrawn from the donor at a rate of ~10–100 ml per minute. Column volumes range from 25–200 ml. Generally the blood is maintained at from 20° C. to 40° C. Below 20° C., cells attach poorly; above 40° C., cell damage also may occur.

Beads can be made with exceptionally smooth surfaces as shown by micrographs. These cells are more easily released from smooth surfaces and thus a higher percentage of the adsorbed cells are recovered. The space between the beads or fibers should be adequate to allow free flow of blood cells whether the bed is expanded or packed. A foraminous support for the beads should have a hole size or mesh opening size above 27 $\mu$m and preferably above 50 $\mu$m to insure free flow of blood therethrough. The cells should become attached to the beads and not physically trapped between the beads. This means that the beads should have a minimum diameter of 90 $\mu$m and preferably a minimum diameter of 200 $\mu$m. When the diameter of the beads is above 400 $\mu$m and particularly when it is above 2000 $\mu$m the available surface area becomes undesirably low and requires the use of an impractical large volume of beads.

Suitable materials for forming the adhering bed should have the following properties.

1. Have a surface to which the cell types of interest will adhere preferentially from whole blood treated with anticoagulants.

2. Be in a form suitable for reproducible packing into suitable containers.

3. Have a softening point of at least 100° and melt above 120° C., or even higher, if sterilization by autoclaving is part of the process. Gumminess and distortion after packing would be unacceptable.

4. Be insoluble in water and aqueous biological media and contain no toxic leachable components.

5. Have a high proportion of its surface smooth (no surface roughness at low magnification, but permitting roughness from cutting cylinders to length).

6. Non-toxic to cells.

7. Resistant to damage during handling.

Generally polyamides, polyacrylates and polyesters are the preferred materials for forming the smooth surfaced substrate for cell adherence.

Polymers useful for beads or spheres whose surfaces are free of angular imperfections, e.g., free from cracks or portions that have a very short radius of curvature, preferably are linear high molecular weight organic polymers that soften above 100° and have a relatively low fluid viscosity when in the molten state. Such readily form smooth surface beads when individual particles of polymers such as short lengths of fibers are heated above the melting point of the polymer in an inert atmosphere and cooled before contacting each other or a hot surface, such as in a shot tower.

Useful thermoplastic polymers include those formed by addition polymerization and copolymerization of olefins, e.g., ethylene, propylene; vinyl halides such as vinyl chloride, vinyl fluoride, vinylidene chloride, vinylidene fluoride, chlorotrifluoroethylene; specific copolymers, e.g., of ethylene with vinyl acetate and/or with carbon monoxide; acrylic polymers and copolymers, e.g., of acrylic or methacrylic acid or esters; acrylonitrile; styrene polymers and copolymers are useful. Also suitable are polyethers such as formed by polymerization and copolymerization of formaldehyde.

Especially useful are polyamides or polyesters having aliphatic or aromatic groups. These include those formed from the reaction of (a) aliphatic diamines of from 4 to 12 carbon atoms with aliphatic diacids of from 4 to 12 carbons, (b) from aliphatic cyclic lactams of from 5 to 12 carbon atoms, (c) from the reaction of piperazine of N,N'-dialkyl substituted aliphatic diamines of from 4 to 12 carbon atoms with aliphatic diacids of from 4 to 12 carbon atoms, (d) from the reaction of aliphatic diamines of from 4 to 12 carbon atoms with aromatic acids such as isophthalic or terephthalic, and (e) copolyamides formed from the reaction of two or more diamines with one diacid or from two or more diacids with one diamine.

Especially preferred are those polyamides known as nylon 6 (polyhexaneamide), nylon 66 [poly(hexamethylene adipamide)], nylon 610 [poly(hexamethylene decaneamide)], nylon 612 [poly(hexamethylene dodecaneamide)], nylon 11 (polyundecaneamide), nylon 12 (polydodecaneamide), and those copolyamides known as nylon 66 + 610 [poly(hexamethylene adipamide + decaneamide)] and nylon (6+66+610) [poly(hexaneamide + hexamethylene adipamide + decaneamide)].

Also useful are the polyesters formed by the reaction of an aliphatic diol from 2 to 10 carbon atoms with terephthalic, isophthalic or phthalic acids, for example, poly(ethylene terephthalate), poly(butylene terephthalate) and poly(1,4-cyclohexanedimethylene terephthalate); poly[4-(2-hydroxyethyl)benzoic acid] and copolymers of ethylene glycol or polyethylene glycol with terephthalic and isophthalic, 4-hydroxybenzoic or 1,2-diphenoxyethane-4,4'-dicarboxylic acids.

Also suitable are polyurethanes derived from the reaction of aliphatic diols from 2 to 10 carbon atoms with aliphatic diisocyanates of from 2 to 10 carbon atoms, or 4,4'-tolylene diisocyanate, or 4,4'-diphenylmethane diisocyanate, or 1,5-(naphthylene diisocyanate); copolymers or capped forms of poly(ethylene adipate), poly(ethylene sebacate), poly(diethylene glycol adipate), poly(ethylene sebacate), poly(diethylene glycol adipate), poly(oxytetramethylene glycol) or trimethylolpropanepropylene oxide copolymer with the above diisocyanates. Polyureas derived from the reaction of aliphatic diamines of from 2 to 10 carbon atoms with the above diisocyanates can be used.

Cellulose esters, for example, cellulose acetate-butyrate can be used for preparation of the spheres, but are not preferred.

Smooth surface spheres are formed from (1) cylinders of desired length cut from fibers; (2) powders of desired sieve size obtained by cryogenically grinding flake or commercial molding pellets and dropping the particles of polymer through a hot zone of inert gas such as helium, argon, or nitrogen. The temperature required will depend on the melting temperature of the particle, the size of the particle, and the length of the heated zone in the "shot tower". A large particle takes longer to melt through than a small particle. This may require increasing the temperature of the heating zone and/or the length of the heating zone to provide more time for melting. For preferred particles for blood cell separation temperatures are from about 200° C. to 950° C. Nylon and polyester spherical beads were usually made with shot tower temperatures of about 300°–375° C. Quenching is readily accomplished with nylon and polyester by having the tower extend 2 to 3 feet or more below the furnace to allow the particles to solidify before they are collected at the bottom of the tower. To facilitate quenching, the inert gas used in the column is fed into the bottom of the tower and out the top of the tower.

The following table shows beads prepared by the general process described but from selected polymers and the type of granule from which they were derived.

TABLE I

| Polymer | Source |
|---|---|
| Low density polyethylene | Ground powder |
| 2G-12 polyester | Powder from dispersion process |
| 2G-12/612 (70/30 mole %) Polyester/polyamide | Powder from dispersion process |
| 6u/610 polyamide | Powder from dispersion process |
| PTMEG Polyurethane | Ground powder |
| Polyformaldehyde | Ground powder |
| Polystyrene | Ground powder |
| Ethylene/methacrylic acid (18%) | Ground powder |
| Polycarbonate 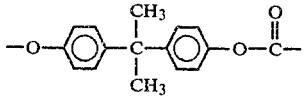 | Ground powder |
| 2G-T polyester | Ground powder |
| 2G-T polyester | Cylinders with l = d cut from fiber |

Inorganic substances such as glass are generally brittle and undesirable for use in bead forms.

One advantage of the present invention is in the recovery of the granulocytes from the beads. When using a pack of tightly packed nylon fibers of the type described in U.S. Pat. No. 3,462,361, which at present is the industry standard, it is necessary to use mechanical energy, i.e., hit the pack against something or strike the pack with something to loosen the granulocytes from the fibers when recovering the leukocytes from the pack. In our process a gentle washing coupled with a physical expansion of the bed serves to remove the leukocytes from the beads without requiring the need for large quantities of eluting solution. The cells are recovered in a concentrated form by simple elution, usually eliminating the need for further concentrating and possible damage to the cells.

A further advantage of beads is that they have regular and smooth adherent surfaces. Bead size can be varied as can cell spreading to provide basis for advantageous high recovery of desired cells.

Present day tightly packed fiber beds wherein the individual fibers usually exhibit high orientation reduce the random trapping of cells during the adherence operation. Subsequent removal of selected cells without physical change of the fibers in eluant liquid is more difficult.

EXAMPLES

A control column is assembled using the nylon fiber (scrubbed 3-denier, 1.4 mil length fiber) which is presently used commercially for filtration leukapheresis. The fibers have a surface area of about 0.18 square meters per gram.

A 3 cc disposable syringe is packed to the 1 cc level with 300–350 mg of fibers by pushing down the fibers with a glass rod (see Items 1, 2, 3 of Table II). The syringe is connected to a peristaltic pump using 1/16 inch (1.6 mm) inside diameter tubing. Other syringes of the same size are used to test the nylon beads and filled to the 1 cc leval; 12 cc syringes are filled to the 2 cc level. When using the nylon fiber-filled syringes the syringes were vertically disposed with the flow being downward. For tests with the nylon beads, the syringes were held at about a 30° angle from vertical to allow the suspension to run down the side of the tube.

The system is operated by placing 80 vol. % of a suitable tissue culture (McCoy's 5A) and 20 vol. % fetal calf serum in a glass beaker (approximately 30 ml) and pumping this through the column and back into the beaker at approximately 2 ml per minute. This procedure is continued for 10–30 minutes with the solution kept at 37° C. Blood is collected in heparin from random donors. The red cells are allowed to settle out of the blood and the leukocyte-enriched plasma is removed and diluted with a mixture of 80 vol. % McCoy's 5A solution and 20 vol. % fetal calf serum to contain approximately $6 \times 10^6$ cells/ml. The column is drained and 10 ml of the diluted suspension of cells is started through the column. The column is run at approximately 2 ml per minute. The liquid level in the column is adjusted to be well above the beads or fiber packing. Some air is left in the column so that the development of a back pressure can be observed. When a back pressure develops in the column, the run is terminated. The columns are run for periods of from 5 to 20 minutes. For each blood sample used tests with different column packings were run side by side for the same period of time. At the end of the adherence period the columns are allowed to drain at the same rate. The columns are then filled with an aqueous solution of ACD (0.73 g citric acid, 2.2. g sodium citrate and 2.45 g dextrose per 100 ml at a pH of 5.0) using the same pump. Twenty-five ml of ACD was passed through the column packed with fibers twice at approximately 2 ml per minute. The columns packed with fiber were tapped during the recovery period. The columns containing beads are filled with ACD with the pump and slowly inverted two times and drained. The cells are then counted and the number of granulocytes or PMN's (polymorphonuclear leukocytes) determined using a Coulter counter, Model ZH, and Channelizer C-1000. The results are reported in Table II.

The nylon beads were prepared by melting polyhexamethylene adipamide cylinders in a "shot tower". The cylinders were obtained by cutting 330-denier 66 nylon filament to lengths of 100–200 $\mu$m. The 330 denier fiber has a diameter of 0.202 mm (202 $\mu$m). The cut granules were then extracted with Freon ® 113 in a Soxhlet apparatus to remove the spin finish on the original fiber. The finish-free granules were made into beads by dropping them down a 58 mm outside diameter quartz tube 1.68 m long in two 18-inch, Hevi Duty split furnace. The furnaces were maintained at a temperature of 500° C. Argon was passed in the bottom of the quartz tube at a rate of 8 ml/min to provide an inert atmosphere and to cool the molten sphere of polymer as it emerged from the furnace. The beads were collected in an aluminum weighing dish at the bottom of the quartz tube. The beads are items 4, 5, 6 while cylinders are 7, 8, 9 of Table II.

The ground nylon referred to in Table II (Items 10, 11) was prepared as follows: 66 Nylon pellets (2.5 mm×2.5 m) were put through a Mikro-Pulverizer fitted with ¼" screen along with solid carbon dioxide used to cool the polymer sufficiently to make it brittle enough to fracture. The ground polymer was then sieved and the material that passed through a 70-mesh sieve but not through a 80 mesh sieve was collected (210–250 $\mu$m). The surface area of the nylon powder was 0.099 m²/g. Micrographs show an average size was 200 $\mu$m. Before use, the granular samples were subjected to scrubbing with dilute hydrochloric acid to insure the surface of the polymer was free of oils or other contaminants.

TABLE II

|   | Material | Doner | Cells Held ($\times 10^6$) | Recovered % | Cells Recovered that are PMN's % | Efficiency % |
|---|---|---|---|---|---|---|
| 1. | Fiber | A | 46 | 61 | 81 | 54 |
| 2. | Fiber | B | 27 | 62 | 71 | 49 |
| 3. | Fiber | C | 36 | 54 | 72 | 41 |
|   |   |   |   | 59 |   | 48 |
| 4. | Nylon Beads | A | 44 | 91 | 87 | 83 |
| 5. | " | B | 24 | 93 | 71 | 66 |
| 6. | " | C | 29 | 88 | 76 | 57 |
|   |   |   |   | 91 |   | 69 |
| 7. | Nylon Cylinders | A | 46 | 80 | 87 | 75 |

TABLE II-continued

| | Material | Doner | Cells Held (× 10⁶) | Recovered % | Cells Recovered that are PMN's % | Efficiency % |
|---|---|---|---|---|---|---|
| 8. | " | B | 24 | 81 | 67 | 54 |
| 9. | " | C | 35 | 72 | 72 | 54 |
| | | | | 78 | | 61 |
| 10. | Ground Nylon | B | 40 | 40 | 43 | 21 |
| 11. | " | C | 45 | 40 | 42 | 23 |
| | | | | 40 | | 22 |

In the above table the % recovery is the number of nucleated cells recovered after elution/the number cells adhered in the column times 100 PMN's is polymorphonuclear leukocytes; efficiency is the total number of PMN's in the recovered cells/the number of PMN's in the original blood samples times 100.

The samples from the individual donors (A, B and C) were run at the same time in parallel with each column so that the results are directly comparable. These comparative runs show that while the beads collect or hold slightly less cells the recovery of the cells from the beads is much higher.

Recovery by expanding the nylon fibers in ACD can increase recoveries to substantially quantitative.

We claim:

1. A process comprising passing blood through an expandable bed packed with synthetic normally solid polymer having a smooth surface and an average diameter of from about 90 μm to about 2000 μm whereby granulocytes become adhered to the packing, expanding the bed from 25% to 600%, and washing the granulocytes off the packing with a physiologically acceptable solution.

2. The process of claim 1 wherein the packing is made of a resin selected from the class consisting of nylon, polymethyl methacrylate, and polyesters.

3. The process of claim 2 wherein the packing is beads or rods.

4. The process of claim 3 wherein the packing is beads, which beads are made of nylon.

5. The process of claim 4 wherein the nylon is poly(-hexamethylene adipamide).

6. The process of claim 5 wherein the beads have an average diameter of from 150 to 400 μm.

7. The process of claim 1 wherein the bed is beads which bed is inverted to wash the granulocytes from the beads.

8. The process of claim 7 wherein the beads are made of a resin selected from the class consisting of nylon, polymethyl methacrylate, and polyesters.

9. The process of claim 8 wherein the beads are made of nylon.

10. The process of claim 9 wherein the nylon is poly(-hexamethylene adipamide).

11. The process of claim 10 wherein the beads have an average diameter of from 150 to 400 μm.

* * * * *